(12) United States Patent
Kita et al.

(10) Patent No.: US 6,834,530 B2
(45) Date of Patent: Dec. 28, 2004

(54) ODOR MEASURING APPARATUS

(75) Inventors: Jun-ichi Kita, Kyoto-fu (JP); Yoshiharu Iwasaki, Saitama-ken (JP); Yoshihiro Aoyama, Kyoto-fu (JP); Hisamitsu Akamaru, Osaka-fu (JP); Hirokazu Taniguchi, Osaka-fu (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 10/367,984

(22) Filed: Feb. 19, 2003

(65) Prior Publication Data

US 2003/0172717 A1 Sep. 18, 2003

(30) Foreign Application Priority Data

Feb. 19, 2002 (JP) .......................................... 2002-041465
Aug. 30, 2002 (JP) .......................................... 2002-254975

(51) Int. Cl.[7] ................................................. G01N 7/00
(52) U.S. Cl. ....................... 73/23.34; 73/23.2; 73/23.34; 73/23.41; 73/31.06
(58) Field of Search ............................ 73/23.2, 23.34, 73/23.41, 31.06

(56) References Cited

U.S. PATENT DOCUMENTS

| | | | | |
|---|---|---|---|---|
| 5,177,994 A | * | 1/1993 | Moriizumi et al. | 73/23.34 |
| 5,541,851 A | * | 7/1996 | Sato et al. | 73/23.21 |
| 6,360,584 B1 | * | 3/2002 | Okubo et al. | 73/23.34 |
| 6,411,905 B1 | * | 6/2002 | Guoliang et al. | 73/31.06 |
| 6,439,026 B2 | * | 8/2002 | Nakano et al. | 73/23.34 |
| 6,494,077 B2 | * | 12/2002 | Aoyama et al. | 73/23.41 |
| 2003/0022082 A1 | * | 1/2003 | Ohmura et al. | 430/105 |

FOREIGN PATENT DOCUMENTS

| | | |
|---|---|---|
| EP | 0950 895 A2 | 10/1999 |
| EP | 0950 895 A3 | 1/2002 |
| JP | 11-352088 | 12/1999 |
| JP | 2000146883 | 5/2000 |
| WO | WO 99/61902 | 12/1999 |
| WO | WO 00 20852 A | 4/2000 |
| WO | WO 00/79243 A1 | 12/2000 |

* cited by examiner

Primary Examiner—Hezron Williams
Assistant Examiner—André K. Jackson
(74) Attorney, Agent, or Firm—Westerman, Hattori, Daniels & Adrian, LLP (57) ABSTRACT

The present invention proposes an odor measuring apparatus capable of determining the similarity of the odor of an unknown sample with high objectivity and performing measurements with sensitivity similar to that of the human nose. According to a mode of the invention, an m-dimensional space is created from detection signals of m pieces of odor sensors, and a standard odor vector S1 representing the result of measurement of a standard odor and another vector Sx representing the result of measurement of an unknown sample are drawn in the space. Then, from the angle θ between the two vectors, a degree of similarity is determined within the range from 0 to 100%, where the degree of similarity is corrected taking account of the difference in sensitivity between the odor sensor and the human nose. The degree of similarity of the unknown odor is calculated for each of plural standard odors measured beforehand, and which standard odor is the closest to the odor of the unknown sample is objectively shown by numeral values.

9 Claims, 8 Drawing Sheets

| | ATOMATIC SERIES | ALCOHOL | HYDRO-CARBON | ESTER |
|---|---|---|---|---|
| RESEMBLANCE | 24 | 35 | 12 | 32 |
| ODOR INDEX | 16.5 | 17.8 | 14.2 | 16.1 |
| ODOR INTENSITY | 3.5 | 3.7 | 2.6 | 3.4 |

| AMINE | ALDEHYDE | SULFUR COMPOUND | ORGANIC ACID | TOTAL |
|---|---|---|---|---|
| 89 | 45 | 45 | 32 | -- |
| 24.2 | 15.5 | 19.5 | 17.5 | 25.2 |
| 4.1 | 3.6 | 3.4 | 3.2 | 4.2 |

| | KILIMAN-JARO | MOCHA | BLUE MOUNTAIN | DOMINICA | GUATEMALA | INTENSITY |
|---|---|---|---|---|---|---|
| RESEMBLANCE | 24 | 35 | 89 | 32 | 12 | 2.7 |

Fig. 16

ODOR MEASURING APPARATUS

The present invention relates to an odor measuring apparatus for measuring and analyzing odors (flavor, fragrance, stench, etc.), which is used for identifying an unknown odor and for measuring its odor intensity. The present invention is applicable to various fields of apparatus such as one for measuring stenches or an apparatus for inspecting and/or evaluating the quality of foodstuffs or medicines.

BACKGROUND OF THE INVENTION

Conventionally, the discernment and evaluation of odors is performed by the olfactory sense of the human being. By this method, it must be considered that different persons (or panels) have different olfactory sensitivities and the olfactory sense of a panel may vary depending on such mitigating factors as mood, alertness, health, etc. of the panel, or on the day of the test. Therefore, to obtain an objective result with high systematic accuracy, it is necessary to gather an adequate number of panels and to conduct the test under an adequately uniform environmental condition. Thus, the test often consumes a lot of time and labor. Further, even under a desirable physical and environmental condition, it is very difficult to obtain a conclusive result based on a fixed standard because the olfactory sense of the human being easily adapts to odor.

One solution to this problem is a flavor and fragrance analyzer as disclosed in the Japanese Unexamined Patent Publication No. H11-352088, an example of which is "FF-1" commercially manufactured by Shimadzu Corporation. The flavor and fragrance analyzer, which has plural odor sensors, calculates the distance (or similarity) between the odors of plural samples based on the detection signals of the odor sensors. The calculation is performed, for example, by multivariate analysis such as cluster analysis or principal component analysis, or by a nonlinear analysis using a neural network.

The above flavor and fragrance analyzer is particularly applicable to the inspection of the quality of foodstuffs, or other analyses where the similarity of plural odors shall be relatively determined within a comparatively narrow range of categories. This analyzer, however, has the following problems:
(1) It is difficult to objectively or absolutely determine the similarity of a wide range of odors, as in the case of the examination of bad odors.
(2) Since the sensitivity of the odor sensor is not always consistent with that of the human nose, the result obtained by the analyzer sometimes differs from that obtained by the organoleptic examination by the olfactory sense.
(3) It is difficult to visually understand the similarity between an odor and plural standard odors.
(4) Even when two odors are discernable, it is often difficult to definitely determine whether they differ in odor intensity or in odor quality.

To solve the above problems, one object of the present invention is to propose an odor measuring apparatus capable of showing the similarity of a various kinds of odors to known standard odors by absolute values. Another object is to propose an odor measuring apparatus capable of discriminating odors like the olfactory sense of the human being.

SUMMARY OF THE INVENTION

Thus, the present invention proposes a first odor measuring apparatus, which includes:

a) m pieces of odor sensors having different responsive characteristics, where m is an integer greater than one (i.e., two or more);
b) an angle calculator for calculating the angle between an unknown odor vector and a standard odor vector in an m-dimensional space formed by the result of a measurement with the m pieces of odor sensors, where the unknown odor vector is represented by the result of a measurement of an unknown sample and the standard odor vector is represented by the result of a measurement of a known standard odor; and
c) an index calculator for calculating an index which represents a similarity of the unknown odor to the standard odor, where the index is calculated based on the angle.

In the measurement of a standard odor with the m pieces of odor sensors, every odor sensor produces an intensity signal, so that m pieces of data are obtained. Mathematically, the m pieces of data can be represented by a point in an m-dimensional space ("sensor's odor space"). When plural standard samples containing the standard odor of different concentrations are measured, the point moves within the sensor's odor space in a certain direction with the change of the concentration. The movement of the point can be defined by a vector called "odor vector" in this specification. The odor vector is specific to the kind of the odor concerned. Therefore, in the sensor's odor space, when the direction of the odor vector obtained by a measurement of a sample containing an unknown odor is close to that of the standard odor vector, the two odors can be determined as similar kinds. In contrast, when the directions of the two odor vectors differs greatly, the two odors are determined as distant kinds.

Thus, in the first odor measuring apparatus, the angle calculator calculates the angle between the standard odor vector and the unknown odor vector as an index for representing the distance between the two vectors. Then, using the angle as the basis, the index calculator calculates an index to be used for determining the similarity of the odor of the unknown sample to the standard odor. For example, the index is determined as a percentage of similarity ranging from 0 to 100%. When the angle is zero, the standard odor and the odor of the unknown sample can be regarded as the same kind, and the percentage of similarity is determined as 100%. When the angle is greater than a preset angle, the standard odor and the odor of the unknown sample are regarded as being totally different kinds, and the degree of similarity is determined as 0%.

Thus, the first odor measuring apparatus can show the similarity of an unknown odor to a standard odor by an absolute value. Therefore, odors can be discriminated more objectively than before, and it is easier to compare plural unknown odors and determine their similarity. Proper selection of plural kinds of standard odors will make it possible to obtain the similarity of an unknown odor to each of the standard odors. Thus, various kinds of odors can be discriminated with adequate accuracy, so that the apparatus can be applied to various fields.

The first odor measuring apparatus may further include an intensity calculator for calculating an index relating to an odor intensity by a method including the following steps: taking the orthogonal projection of the unknown odor vector on the standard odor vector; deriving the odor concentration of the standard odor vector component of the unknown sample from the length of the orthogonal projection of the unknown odor vector; and calculating the index relating to the odor intensity. Such a construction makes it possible to obtain not only the similarity of the odor of an unknown sample to the standard odor but also the odor intensity, odor index or the like.

In a preferable mode of the invention, the index calculator includes a corrector for correcting the index, taking account of the difference in sensitivity between the odor sensor and the olfactory sense of the human being. Such a construction makes the measurement result free from the influence due to the difference in the sensitivity between the odor sensor and the olfactory sense of the human being, where the result becomes more natural to the sense of the human being. Thus, the apparatus according to the present invention becomes more suitable as an alternative to organoleptic examination.

Further, the first apparatus may include a storage unit for pre-storing results of measurements of n kinds of standard odors by the odor sensors, where n is an integer greater than one (i.e., two or more), or for pre-storing standard odor vectors represented by the results of the measurements.

By this construction, plural kinds of standard odors are measured beforehand, and the results of the measurements are stored in the storage unit. After that, a measurement of only an unknown sample is necessary to objectively discriminate or evaluate the odor of the unknown sample. In particular, the odor of an unknown sample can be properly indicated by plural indices of similarity. Further, the apparatus may include a display for visually showing the plural indices of similarity. This construction helps an intuitive understanding of the result of the measurement, so that even those who are not skilled in odor analysis can use the apparatus without difficulty.

The present invention further proposes a second odor measuring apparatus which includes:

a) m pieces of odor sensors having different responsive characteristics, where m is an integer greater than one (i.e., two or more);
b) a concentration point locator for locating a temporary point of concentration on a standard odor curve in an m-dimensional space formed by the result of measurement with the m pieces of odor sensors, where the standard odor curve is represented by the result of a measurement of a known standard odor, and the temporary point of concentration is located by a preset rule with respect to a measurement point representing the result of a measurement of an unknown sample; and
c) an index calculator for calculating an index representing the similarity of the unknown odor to the standard odor, where the index is calculated based on the location of the temporary point of concentration in the m-dimensional space and on a value representing an index of proximity of the temporary point of concentration to the measurement point.

When plural standard samples with different concentrations of the same standard odor are measured, the measurement points of these samples are located apart from each other due to the difference in the concentration of the standard odor. These measurement points form a curve (or a straight line in some cases) corresponding to the standard odor. The points on this curve (called the "standard odor curve" in this specification) correspond to different concentrations of the standard odor.

In the second apparatus, the concentration point locator follows a preset rule to locate a temporary point of concentration on the standard odor curve corresponding to the measurement point representing the result of the measurement of an unknown sample. The temporary point of concentration can be regarded as indicative of the concentration of the odor measured on the assumption that the odor of the unknown sample contains only the standard odor. When the measurement point of the unknown sample is not located on the standard odor curve, the degree of contribution of the standard odor to the odor of the unknown sample can be regarded to depend on the proximity of the measurement point to the temporary point of concentration within the space. Thus, the index calculator estimates the odor concentration from the location in the space of the temporary point of concentration and the degree of contribution of the standard odor from the index of proximity, and then calculates the index for determining the similarity of the unknown odor to the standard odor.

Thus, the second odor measuring apparatus can show the similarity of an unknown odor to a standard odor by an absolute value. Therefore, odors can be discriminated more objectively than before, and it is easier to compare plural unknown odors and determine their similarity. Proper selection of plural kinds of standard odors will make it possible to obtain the similarity of an unknown odor to each of the standard odors. Thus, various kinds of odors can be discriminated with adequate accuracy, so that the apparatus can be applied to various fields.

In a mode of the present invention, the concentration point locator locates the temporary point of concentration as the point on the standard odor curve where the distance from the measurement point is minimized. The index calculator attenuates the concentration, derived from the location in the space of the temporary point of concentration, according to the distance between the temporary point of concentration and the measurement point, or according to the angle between a standard odor line and an unknown odor line drawn on the assumption that each of the standard odor and the unknown odor changes along a straight line with respect to concentration. The index calculator then calculates the index regarding the attenuated concentration as indicative of the contribution of the standard odor to the odor of the unknown sample.

The above distance changes with the odor intensity even when the odor is of the same kind. Therefore, when the degree of attenuation is determined based on the distance, it is preferable to reduce the influence of the odor intensity by, for example, correcting the distance considering the odor intensity.

The index calculator may preferably include a corrector for performing a correction taking account of the difference in sensitivity between the odor sensor and the olfactory sense of the human being, using the threshold of the olfactory sense of the human being. This construction makes the result of the measurement or discernment of an odor consistent with the olfactory sense of the human being.

Similar to the first apparatus, the second apparatus may further include a storage unit for pre-storing the results of measurements of n kinds of standard odors by the odor sensors, where n is an integer greater than one, or for pre-storing standard odor vectors represented by the results of the measurements. This construction provides the same effect as described above regarding the storage unit of the first odor measuring apparatus.

By a further preferable construction, the storage unit stores the standard odor curve in association with information about the measurement date of the standard odor, and the concentration point locator locates the temporary point of concentration on the standard odor curve by using a standard odor curve of the latest measurement date. By this construction, the accuracy of the measurement is improved in the case where several kinds of standard odors are used because the latest results of the measurements of the standard odors can be always used for a measurement of an unknown sample even when the measurements of the standard odors are not conducted continuously or on the same day.

DETAILED DESCRIPTION OF PREFERRED EMBODIMENTS

First Embodiment

An embodiment of the first odor measuring apparatus according to the present invention is described referring to the attached drawings.

Figure 1:
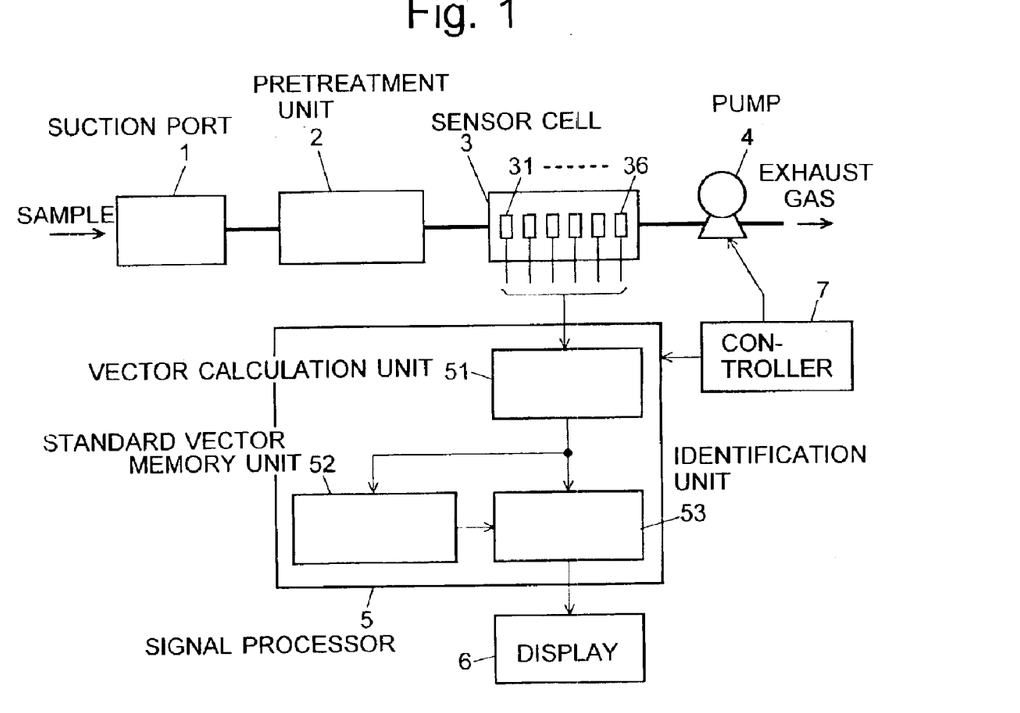
FIG. 1 shows a block diagram of an embodiment of the first odor measuring apparatus as the first embodiment of the present invention.

As shown in FIG. 1, the odor measuring apparatus of the first embodiment includes the following elements: a suction port 1 for sucking a sample; a pretreatment unit 2 for performing a pretreatment of the sucked sample; a sensor cell 3 with six odor sensors 31–36 having different response characteristics for measuring an unknown sample or a standard sample containing a standard odor component; a pump 4 for drawing the unknown sample or the standard sample into the sensor cell 3; a signal processor 5 for analyzing detection signals of the odor sensors 31–36; a display 6 for displaying the results of the analysis; and a controller 7 for controlling the general operation of the apparatus.

The pretreatment unit 2 performs the removal of moisture content from the sample, the condensation or dilution of the sample, the removal of interfering gases, etc. Such pretreatments, however, may be omitted in some cases. The odor sensors 31–36 are, for example, sensors using metal oxide semiconductors whose resistance varies depending on the kinds of odor components. Other examples of the odor sensor include: a sensor using conducting polymers; a sensor using quartz resonators or SAW (surface acoustic wave) devices coated with a gas absorption film. The signal processor 5 and the controller 7 are constructed using a personal computer as a main part. Running of a predetermined program on the personal computer makes the computer to function as a vector calculation unit 51, a standard vector memory unit 52, an identification unit 53, etc.

The measurement principle of the odor measuring apparatus with the above-described construction is described. With this odor measuring apparatus, a standard sample containing plural kinds of odor components are measured beforehand. The standard sample is prepared by mixing and diluting gasified materials taken from gas cylinders or generated from liquids or solids. When a material that gasifies at room temperatures is used, the material is stored in a gas cylinder and taken from there in preset amounts. When a liquid is used, the liquid is put in a glass container or the like, which is then kept at a preset temperature or subjected to a bubbling process with nitrogen gas to generate an odor. When a solid is used, the solid is kept at a preset temperature to generate an odor.

The standard sample prepared as described above is supplied to the suction port 1, and is then drawn into the sensor cell 3 by the pump 4. When the standard sample introduced into the sensor cell 3 contacts the odor sensor 31–36, the odor sensors 31–36 generate respective detection signals in parallel. Accordingly, the signal processor 5 produces six measurement data DS1–DS6 for one standard sample. In a six-dimensional space ("sensor's odor space") formed by six axes corresponding to the detection outputs of the six odor sensors 31–36, a point (DS1, DS2, DS3, DS4, DS5, DS6) represents the six measurement data.

Figure 2:
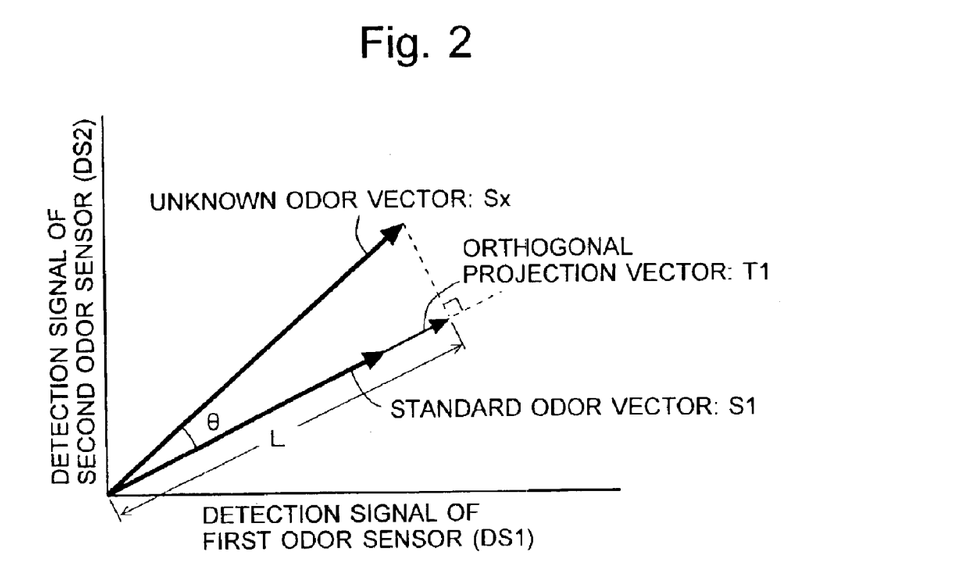
FIG. 2 illustrates the measurement principle of the apparatus of the first embodiment.

The six-dimensional space is difficult to illustrate in a drawing. For the convenience of understanding, a two-dimensional odor space formed by the detection signals DS1, DS2 of the two odor sensors is considered hereby, as shown in FIG. 2. In this two-dimensional space, a point (DS1, DS2) represents two measurement data of one standard sample obtained by the two odor sensors.

When the standard sample is measured while the concentration of the standard odor is changed, the point (DS1, DS2, DS3, DS4, DS5, DS6) moves within the six-dimensional space in a particular direction corresponding to the kind of the odor. The movement of the point can be represented by a vector in the space. Accordingly, a vector (called the "odor vector" hereinafter) S1 is drawn in the two-dimensional space shown in FIG. 2. The direction of the odor vector depends on the kinds of odor. When the measurement is performed for the other standard odor, another odor vector having a direction different from that of the odor vector S1 will be drawn in the two-dimensional space of FIG. 2.

When the measurement is performed for an unknown sample of interest, an odor vector Sx is drawn in the two-dimensional space of FIG. 2. If the direction of the odor vector Sx is close to that of the standard odor vector S1, the odor of the unknown sample and the standard odor can be regarded as close in kind. If, on the other hand, the directions of the two odor vectors differ greatly, the two odors can be regarded as distant kinds. From this idea, the angle θ between the standard odor vector S1 and the odor vector Sx of the unknown sample is used as an index for determining the closeness of the two vectors S1 and Sx, and a degree of similarity is defined based on the angle θ. In concrete terms, the degree of similarity is defined as 100% when the odor vector Sx of the unknown sample coincides with the standard odor vector S1, or when their directions are the same. The degree of similarity, on the other hand, is defined as 0% when no similarity is observable between the two vectors. Thus, the degree of closeness or distance of the odor of an unknown sample to the standard odor is represented by the degree of similarity ranging from 0 to 100%.

In the process of determining the degree of similarity from the angle θ, a correction is made to cancel the difference in sensitivity between the odor sensor and the olfactory sense of the human being. The basic idea of the correction is to emphasize the similarity for such a standard odor for which the olfactory sense of the human being has a low threshold.

Figure 4:
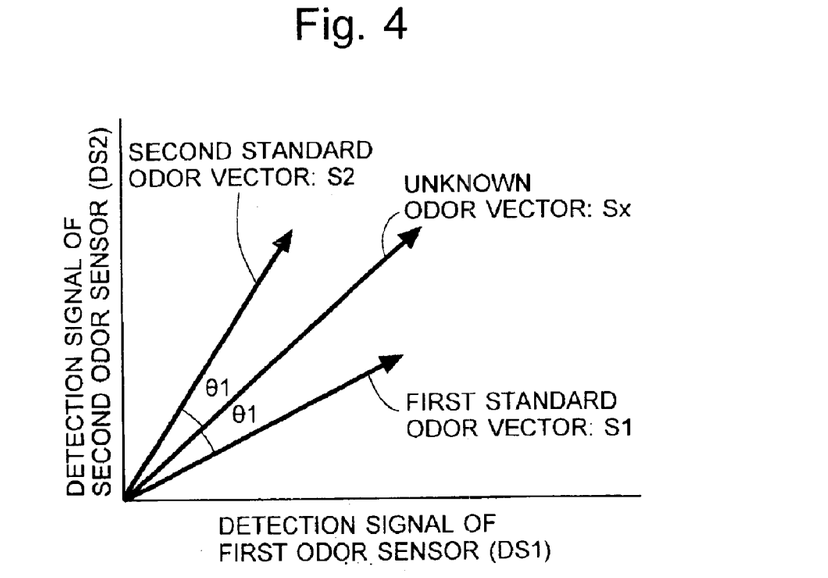
FIG. 4 illustrates the measurement principle of the apparatus of the first embodiment.

For example, it is assumed that the odor vector Sx of an unknown odor makes the same angle θ1 with each of the first standard odor vector S1 and the second standard odor vector S2, as shown in FIG. 4. In this case, the initial determination by the measurement with the odor sensors is that the unknown odor has an equal degree of similarity to each of the first and second standard odors. It is further assumed hereby that an organoleptic examination by the olfactory sense of the human being has proved that the threshold concentration of the olfactory sense of the human being for the first standard odor is half as high as that for the second standard odor. This means that the sensitivity of the olfactory sense of the human being to the first standard odor is twice as high as that to the second standard odor. Under the above conditions, a method of canceling the difference in sensitivity between the odor sensor and the olfactory sense of the human being is to double the similarity to the first standard odor. Such a correction yields a result of identification of the odor similar to the result obtained by the olfactory sense of the human being, irrespective of the kind of odor.

Since the degree of difference in sensitivity between the odor sensor and the olfactory sense of the human being greatly depends on the category of odors and other factors, the extent of correction should be appropriately determined according to the kinds of standard odors selected and other factors.

The odor intensity of an unknown sample is determined as follows. As shown in FIG. 2, an orthogonal projection of the odor vector Sx of the unknown sample on the standard odor vector S1 is taken, and the concentration of the standard vector corresponding to the length of the projection vector T1 is defined as the concentration of the standard odor component contained in the unknown sample. From the concentration thus obtained, the odor index and the odor intensity can be derived because the relations of the concentration of the standard odor with respect to the odor index and the odor intensity are known beforehand. For example, when a maximum value model is adopted to determine the total odor intensity of the unknown sample, the maximum value of the intensities of the standard odor components is selected as the odor intensity of the unknown sample. When a total value model is adopted, the odor indices of the standard odor components are converted to odor concentrations, and the odor index of the odor of the unknown sample is derived from the total value of the odor concentrations.

When there is a linear relation between the detection signal of the odor sensor 31–36 and the concentration of the odor component, the odor vector takes a linear form, as shown in FIG. 2. When, on the contrary, the relation between the detection signal of the odor sensor 31–36 and the concentration of the odor component is nonlinear, the odor vector of a standard sample containing a standard odor and the odor vector of an unknown sample does not take a linear form but a curved form in the six-dimensional (or two-dimensional) space. Even in such a case, the above-described measurement principle serves as a basis for calculating the degree of similarity as follows.

Figure 3:
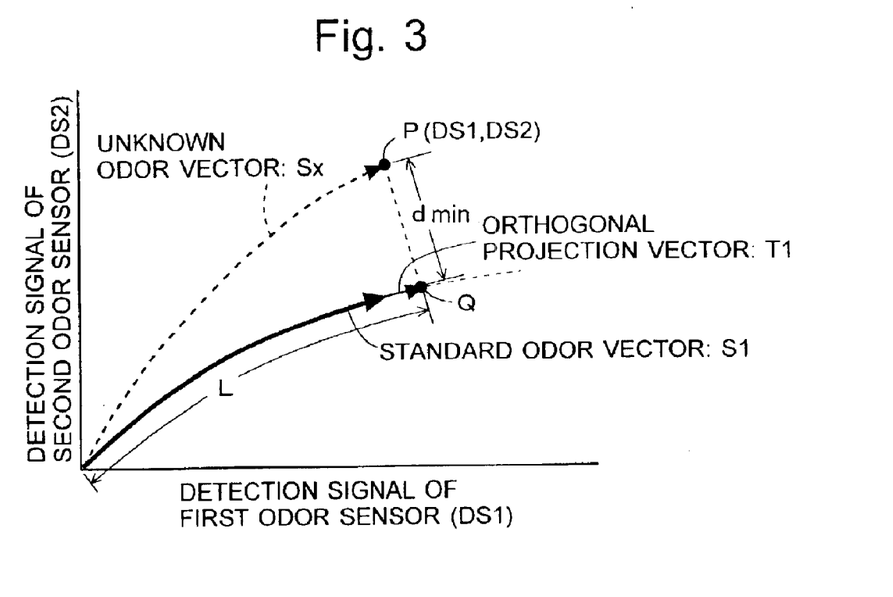
FIG. 3 illustrates the measurement principle of the apparatus of the first embodiment.

It is assumed that a measurement point P(DS1, DS2) of an unknown odor having a certain concentration is located in a two-dimensional space where a curved standard odor vector S1 is drawn as shown in FIG. 3. First, the minimum distance dmin from the measurement point P of the unknown odor to the standard odor vector S1 and the location (or coordinates) of the point Q that gives the minimum distance dmin are determined. In this case, using the length L of the curved vector from the original position to the point Q and the minimum distance dmin, the degree of similarity α of the unknown odor to the standard odor is defined as follows:

$$\alpha = \tan(dmin/L).$$

The measurement operation of the odor measuring apparatus of this embodiment is described below.

As explained above, plural standard odors are measured beforehand to prepare plural standard odor vectors for determining the similarity of unknown odors. For example, eight kinds of standard odors are generated one after another, each of which is introduced into the sensor cell 3 with its concentration changed and is measured by the six odor sensors 31–36. The vector calculation unit 51 creates a different odor vector for each of the standard odors. As a result, the above measurement yields eight standard odor vectors S1–S8 having different directions. The data for constructing the eight standard odor vectors S1–S8 are stored in the standard vector memory unit 52 before the measurement of an unknown sample.

The standard odors may be selected as desired according to the odor to be measured. For a general-purpose apparatus for measuring powerful odors, good odors and bad odors are used as the standard odors. Examples of good standard odors include: aromatic series (e.g. toluene), alcohols (e.g. n-butanol), hydrocarbons (e.g. heptane) and esters (e.g. acetic ester). Examples of bad standard odors include: amines (e.g. trimethylamine), aldehydes (e.g. butyraldehyde), sulfur compounds (e.g. methyl mercaptan) and organic acids (e.g. butyric acid).

In the measurement of an unknown sample of interest, the unknown sample is supplied to the suction port 1, and is then drawn into the sensor cell 3 by the pump 4. Six detection signals produced by the odor sensors 31–36 are sent to the signal processor 5, which determines an unknown odor vector Sx in the six-dimensional odor space. The data that constitutes the unknown odor vector are sent to the identification unit 53.

The identification unit 53 reads out the data constituting the plural standard odor vectors from the standard vector memory unit 52, calculates the angles θ1–θ8 that the unknown odor vector makes with the standard odor vectors S1–S8, respectively, and derives the degrees of similarity, α1–α8, from the angles θ1–θ8 for the standard odors, respectively. Further, the identification unit 53 calculates the orthogonal projections T1–T8 of the unknown odor vector of the unknown sample on the standard odor vectors S1–S8, and derives the odor index and the odor intensity from the lengths of the orthogonal projections T1–T8. Accordingly, when there are eight standard odors used, the odor index and the odor intensity are calculated for each of the eight standard odors.

The signal processor 5 shows the degrees of similarity and other values in an easy-to-understand form on the screen of the display 6. For example, the values are shown in the form of a web graph. More examples will be described later. Such a visual presentation of the values makes it easy for the user to find what standard odor the odor of the unknown sample is similar to or what standard odors the odor of the sample contains as components.

The degrees of similarity obtained as a result of the measurement of an unknown sample may be stored in a memory unit for future use. For example, if the degrees of similarity obtained by a measurement of another unknown sample are the same as the degrees of similarity of the unknown sample stored in the memory unit, the odors of the two samples can be regarded as the same kind. Thus, the apparatus of this embodiment can be used to determine the similarity of two or more unknown samples.

Examples of measurements by the odor measuring apparatus of the first embodiment are explained below.

[Example of Measurement 1]

In this example, the odor measuring apparatus of the first embodiment is applied to the measurement of a stench. As a preferable combination of standard odors for the measurement of stenches, the following eight standard odors are used: four good odors including a aromatic series (toluene), an alcohol (n-butanol), a hydrocarbon (heptane) and an ester (acetic ester); four bad odors including an amine (trimethylamine), an aldehyde (butyraldehyde), a sulfur compound (methyl mercaptan) and an organic acid (butyric acid).

Figure 5:
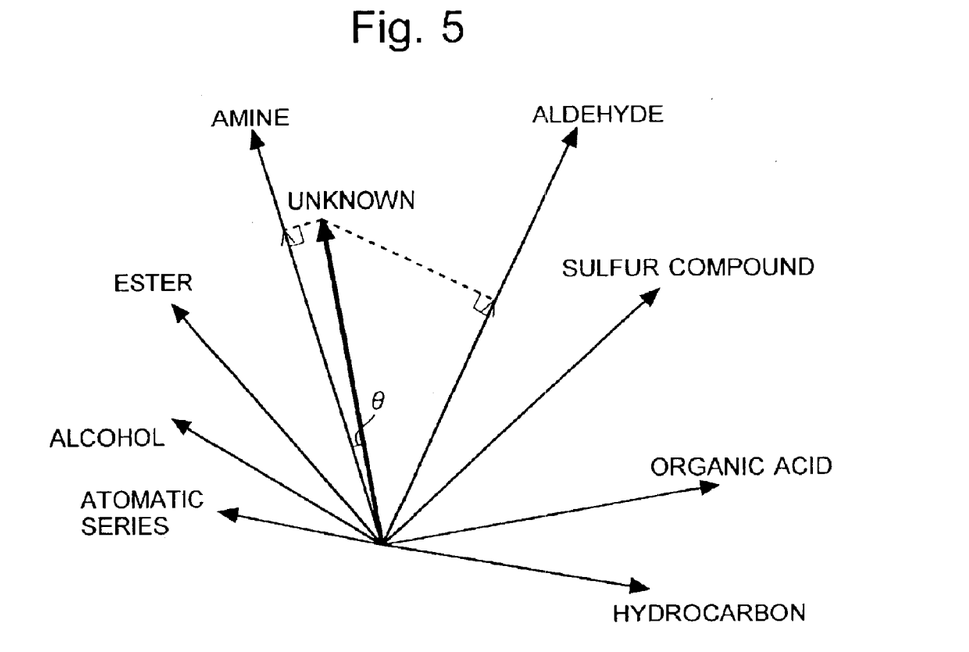
FIG. 5 conceptually shows an example of odor vectors arranged in a six-dimensional space created by the apparatus of the first embodiment.
Figure 6:
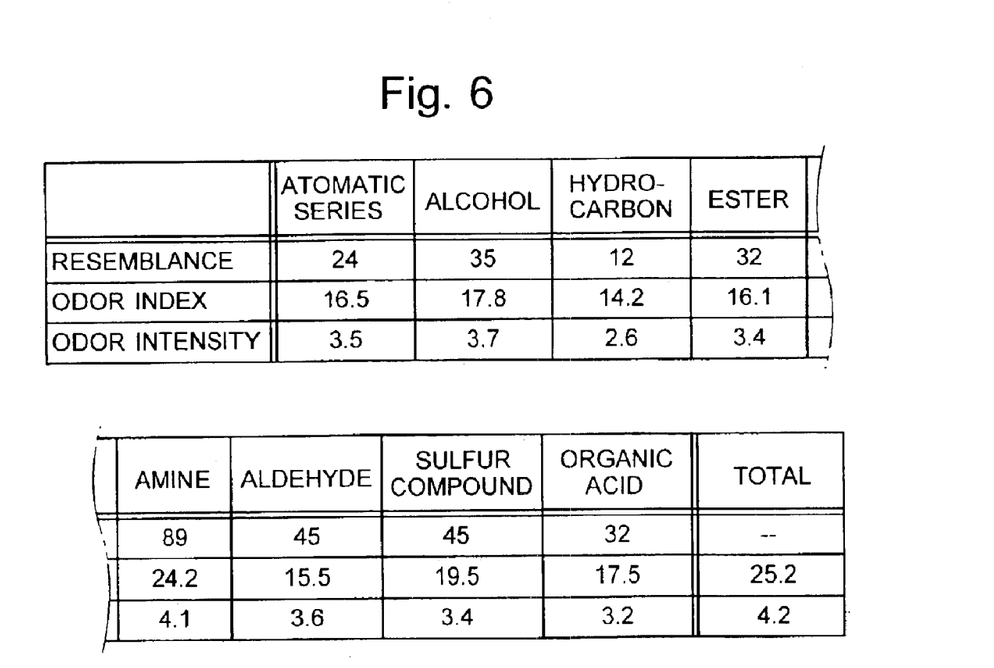
FIG. 6 shows an example of a table showing the results of measurements obtained by the apparatus of the first embodiment.
Figure 7:
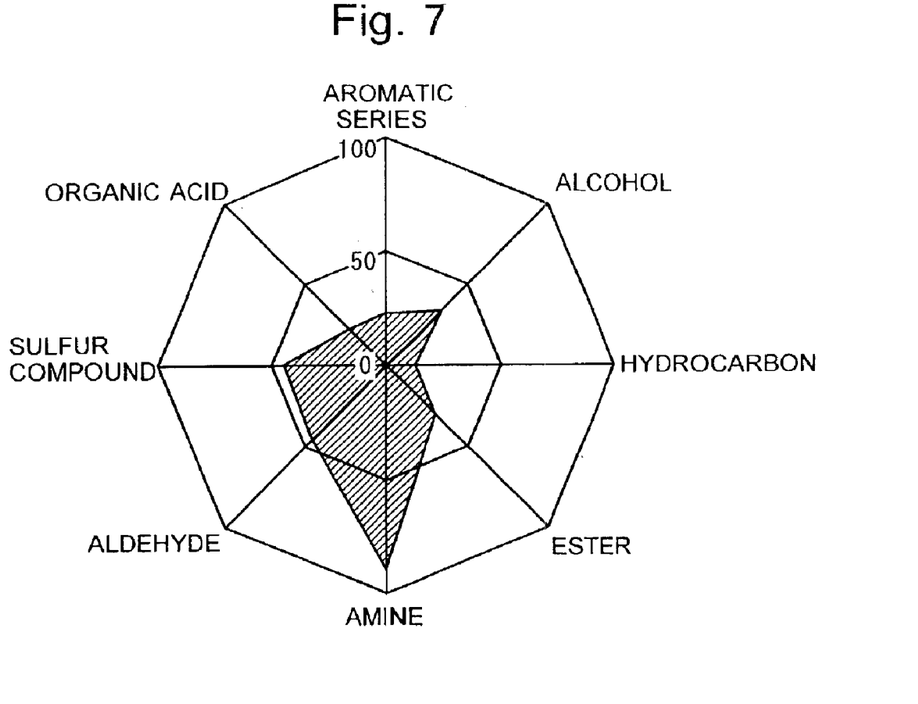
FIG. 7 shows an example of a graph showing the results of measurements obtained by the apparatus of the first embodiment.

FIG. 5 shows a six-dimensional odor space showing the results of the measurements of the above eight standard odors and an unknown sample. FIG. 6 shows a table showing the result of the above-described identification process using the odor vectors, where the degree of similarity, odor index and odor intensity of the odor of the unknown sample is shown for each standard odor. A simple presentation of this table will make it easy to understand that the odor of the unknown sample is close to amine because its degree of similarity is high. To further help the intuitive understanding, a web graph as shown in FIG. 7 is displayed on the screen of the display 6. This graph makes it possible to understand with a single glance that the odor of the unknown sample is close to amine. Further, what odor other than amine has a high degree of similarity can be intuitively understood.

[Example of Measurement 2]

Figure 8:
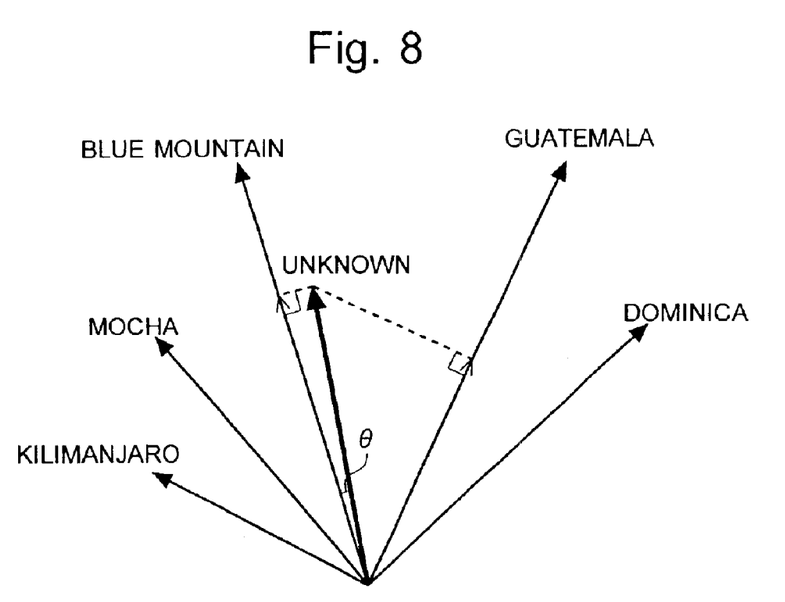
FIG. 8 conceptually shows an example of odor vectors arranged in a six-dimensional space created by the apparatus of the first embodiment.

In this example, the odor measuring apparatus is applied to the inspection of different fragrances of coffee. The following five kinds of coffee are used as the standard odors: Kilimanjaro, Mocha, Blue Mountain, Dominica and Guatemala. It should be noted that other kinds of coffee may be used as the standard odor. FIG. 8 shows a six-dimensional odor space showing the results of the measurements of the above five standard odors and an unknown sample. The degrees of similarity to the standard odors are determined by the above-described identification process using odor vectors.

In the case of measuring a fragrance of a foodstuff like coffee, the relation of the concentration of the standard odor component to the odor index or to the odor intensity is not definitely known. Therefore, even when the concentration is derived from the length of the orthogonal projection, it is difficult to directly derive the odor index or the odor intensity from the concentration. Taking account of this problem, a predetermined conversion formula has been prepared to determine which of six degrees of odor intensity applies to the odor of interest, where the six degrees of odor intensity are as follows:

Intensity 0 (Odorless.)
Intensity 1 (Odor detectable but its kind not identifiable.)
Intensity 2 (Odor detectable and its kind identifiable.)
Intensity 3 (Odor of normal intensity.)
Intensity 4 (Strong odor.)
Intensity 5 (Very strong odor.)

The conversion formula may be prepared by various methods. One method is as follows: find a standard odor for which the relations of the odor concentration to the odor index and to the odor intensity are known and which is the closest to the odor of interest (i.e. fragrance of coffee for the present example), and prepare a conversion formula based on those relations of the odor concentration to the odor index and to the odor intensity, where the relations may be modified if necessity.

Figure 9:
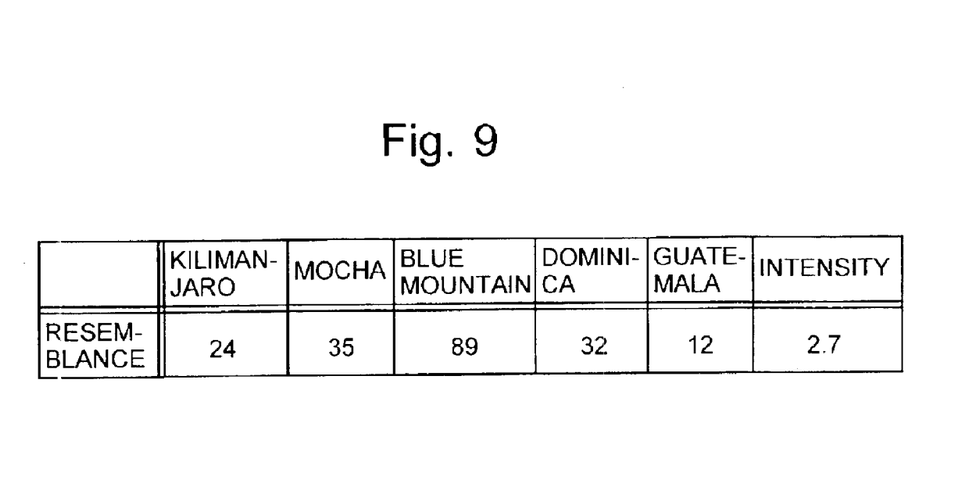
FIG. 9 shows an example of a table showing the results of measurements obtained by the apparatus of the first embodiment.
Figure 10:
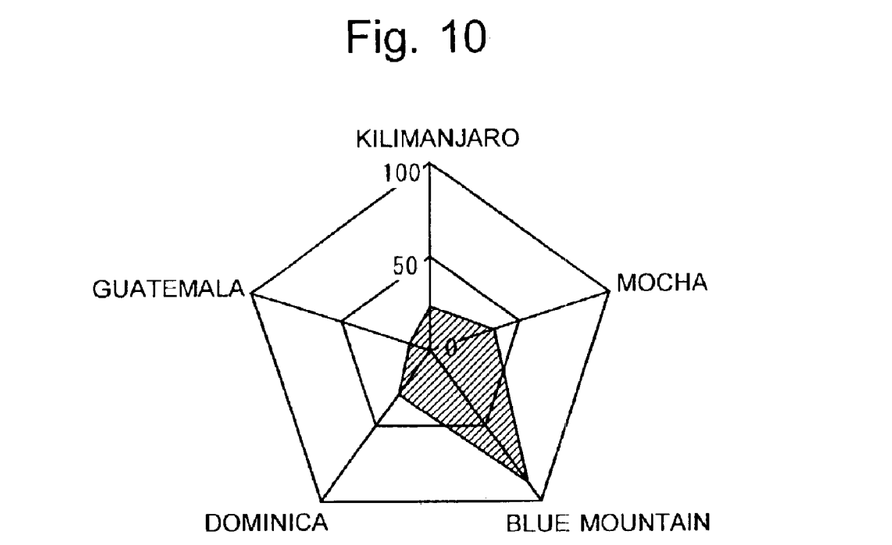
FIG. 10 shows an example of a graph showing the results of measurements obtained by the apparatus of the first embodiment.

FIG. 9 shows the degrees of similarity and the odor intensity derived from the above odor vectors, and FIG. 10 shows the web graph of the degree of similarity. These drawings show that the fragrance of the unknown sample is close to Blue Mountain, and the intensity of the fragrance is about 2.7.

Thus, the odor measuring apparatus of the first embodiment can identify odors of any category with high objectivity by properly selecting plural standard odors according to the category of the odor of interest.

Second Embodiment

An embodiment of the second odor measuring apparatus according to the present invention is described referring to the attached drawings.

Figure 11:
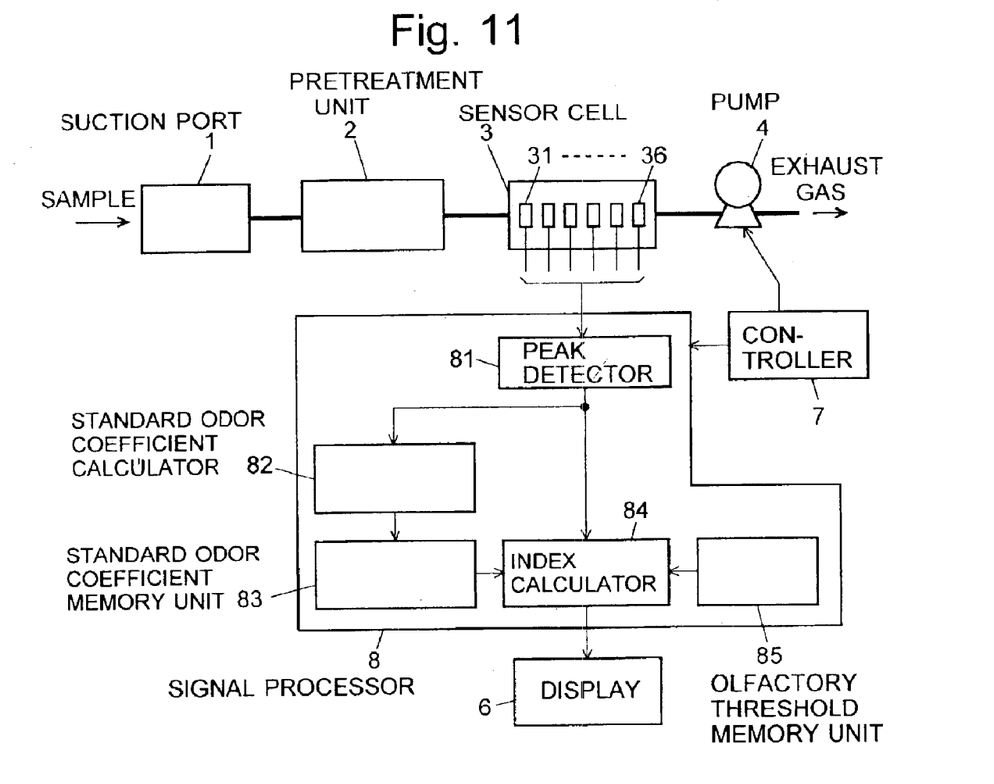
FIG. 11 shows a block diagram of an embodiment of the second odor measuring apparatus as the second embodiment of the present invention.

FIG. 11 is a block diagram showing the construction of the odor measuring apparatus of the second embodiment. This odor measuring apparatus is constructed identical to that of the first embodiment except for the signal processor 8. Accordingly, the same numerals as used in the first embodiment are given to the identical elements and details of such elements will not be described. The signal processor 8, which is constructed using mainly a personal computer, has the following functional blocks: a peak detector 81, a standard odor coefficient calculator 82, a standard odor coefficient memory unit 83, an index calculator 84 and an olfactory threshold memory unit 85.

The measurement principle of the odor measuring apparatus of the second embodiment is described. For the convenience of understanding, a two-dimensional odor space formed by the detection signals DS1, DS2 of the two odor sensors is considered hereby, as shown in FIG. 12.

First, six standard samples are prepared, including three samples containing a first kind of standard odor by different concentrations of C1 [ppm], C2 [ppm] and C3 [ppm], and the other three samples containing a second kind of standard odor by different concentrations of C1 [ppm], C2 [ppm] and C3 [ppm], where C1, C2 and C3 are positive real number satisfying C1<C2<C3. The six standard samples are measured by two odor sensors to obtain detection signals. As explained above, the two detection signals corresponding to one standard sample is represented by a point (i.e. measurement point) in the two-dimensional space, as shown in FIG. 12.

Figure 12:
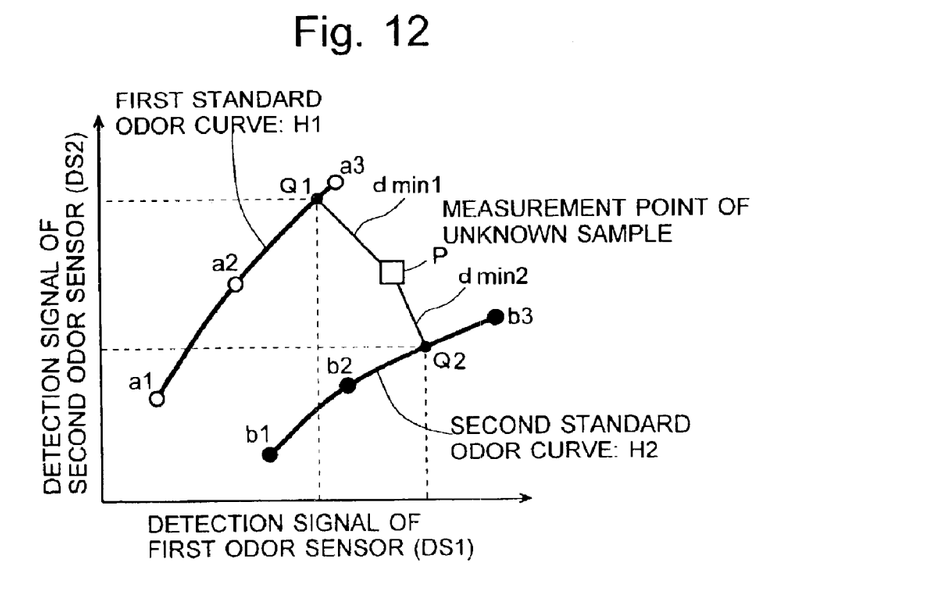
FIG. 12 illustrates the measurement principle of the apparatus of the second embodiment.

In FIG. 12, the measurement points a1, a2 and a3 correspond to the standard samples containing the first standard odor by C1, C2 and C3 of concentration, and the measurement points b1, b2 and b3 correspond to the standard samples containing the first standard odor by C1, C2 and C3 of concentration. For each kind of standard odor, the measurement points (a1, a2 and a3; b1, b2 and b3) are located apart from each other due to the difference in the concentration of the standard odor. From these measurement points, two standard odor curves H1, H2 are drawn corresponding to the two standard samples. The standard odor curve is substantially identical to the standard odor vector in the first embodiment. It is not called "vector" but "curve" because the direction of the line is not considered in this embodiment. As explained above, the odor curve substantially becomes a straight line when there is a linear relation between the output of the odor sensor and the odor concentration.

The odor measuring apparatus of the second embodiment derives the standard odor curves from the measurement points obtained by measuring the standard samples, and stores the data that represents the curve. For example, the standard odor curve is represented by a function using the concentration as an independent variable, and the coefficients of the function are calculated by linear regression analysis or multiple regression analysis based on plural measurement points. In this case, the coefficients of the function are chosen as the data that represents the standard odor curve. It is of course allowable to use a different type of data that represents the standard odor curve in a different form.

Next, an unknown sample of interest is measured in the same manner. This measurement gives a measurement point P located in the two-dimensional space where the standard odor curves H1, H2 are drawn, as shown in FIG. 12. On the assumption that the odor contained in the unknown sample can be represented as a composition of the two kinds of standard odors, the degree of similarity is hereby defined as the degree of contribution of each standard odor to the unknown odor. Here, the degree of each standard odor (such as odor index) should be taken into account.

In concrete terms, two straight lines are drawn from the measurement point P of the unknown sample to two points Q1, Q2 on the two standard odor curves H1, H2, where the Q1 and Q2 are chosen so that PQ1, PQ2 correspond to the minimum distance from the point P to the curves H1, H2, respectively. Each point on the standard odor curve H1 or H2 corresponds to a certain concentration of the standard odor concerned. Therefore, the locations (or coordinates) of the points Q1, Q2 indicate some concentrations of the two standard odors. The location of the point Q1 or Q2 is hereby regarded as indicative of a concentration CH1 or CH2 in the case where the unknown odor is composed of only the first or second standard odor. In practice, however, the contributions of the standard odors to the unknown odor are smaller than the concentrations CH1, CH2 indicated by the points Q1, Q2 because the measurement point P is apart from the standard odor curves H1, H2. The extent of attenuation of the concentration depends on the distance between the point P and the curve H1 or H2. This is the reason why the points Q1, Q2 are called the "temporary" points of concentration.

Given the minimum distance from the measurement point P (DS1, DS2) to the standard odor curves H1, H2 as dmin1, dmin2, the magnitude of the detection signal LS is hereby defined as follows:

$$LS = \sqrt{DS1^2 + DS2^2}. \quad (1)$$

Also, the index ISi (i=1 or 2) for the first and second standard odor is defined as follows:

$$ISi = \tan^{-1}\left(\frac{dmini}{LS}\right). \quad (2)$$

The minimum distance dmin1 is divided by the magnitude of the detection signal LS to normalize the minimum distance by the odor intensity. This normalization cancels the shift of the distance between the measurement point and the standard odor curve, which occurs depending on the odor intensity even when the kind of odor is the same.

When Formula (2) gives the result of IS1=0, the unknown odor is identified as the first standard odor. In this case, the concentration of the first standard odor is CH1 [ppm], as indicated by the temporary point of concentration Q1, and the concentration of the second odor is zero [ppm]. When, on the other hand, IS1≠0, the unknown odor contains both the first and second standard odors. It is assumed hereby that the two standard odor curves H1, H2 were two straight lines forming an angle θ with each other. Then, when the angular position of the measurement point P with respect to the first standard odor curve H1 as the base axis is zero, it means that the unknown odor contains only the first standard odor. When the angular position is θ, it means that the unknown odor contains only the second standard odor.

That is, it can be said that the greater the angle with respect to the base axis (e.g. the first standard odor curve H1) is, the lower the actual content of the standard odor in the unknown sample is. Accordingly, for example, a linear attenuation factor β can be given as follows:

$$\beta = (-1/\theta) \times ISi + 1 \quad (3)$$

where i=1 or 2.

With this equation, the concentrations of the first and second standard odors contributing to the unknown odor are given as follows.

Concentration of standard odor: $CHi' = CHi \times \beta$ \quad (4)

It should be noted that different substances having the same concentration do not always give the same degree of odor perception to a human being. That is, there is a difference in sensitivity between the odor sensor and the olfactory sense of a human being. Therefore, taking account of the characteristics of the olfactory sense of a human being, a correction process is included in the calculation of the degree of similarity, γi, of the unknown odor to the standard odor. Equation (5) shown below is a correction equation using the olfactory threshold Ei (i=1 or 2) indicative of the lowest concentration of the standard odor that the human nose can sense.

$$\gamma i = 10 \times \text{Log}\left(\frac{CHi'}{Ei}\right) \quad (5)$$

Equation (6) gives an index δ indicative of the total odor intensity of the unknown odor.

$$\delta = 10 \times \text{Log}\left[\left(\frac{CH1'}{E1}\right) + \left(\frac{CH2'}{E2}\right)\right] \quad (6)$$

The above example assumed that there are two standard odors. In a more general case where j kinds of standard odors are used, the above angle θ may be replaced by the average of plural angles that the standard odor curves make with each other. In this case, the degree of similarity to the jth standard odor, γj, is given by $$\gamma j = 10 \times \text{Log}\left(\frac{CHj'}{Ej}\right),$$

and the index of the total odor intensity is given by $$\delta = 10 \times \text{Log}\left[\Sigma\left(\frac{CHj'}{Ej}\right)\right]$$

The measurement operation of the odor measuring apparatus of this embodiment is described below.

As explained above, plural standard odors are measured beforehand to prepare plural standard odor curves for determining the similarity of unknown odors. For example, four kinds of standard odors are generated one after another, each of which is introduced into the sensor cell 3 with its concentration changed and is measured by the six odor sensors 31–36. When a standard sample is introduced into the sensor cell 3, the output of each sensor 31–36 varies during a certain time period including the point of introduction. There, the peak detector 81 detects the maximum point (i.e. peak) of the varying output, and chooses the output at that moment as the detection signal. It is of course possible to determine the magnitude of the detection signal by other methods, such as using the area of the peak.

The standard odor coefficient calculator 82 receives the detection signals of the six odor sensors 31–36 from the peak detector 81, and calculates the coefficients of each function that represents a standard odor curve of each standard odor concerned, using detection signals corresponding to each standard odor. The coefficients are stored in the standard odor coefficient memory unit 83. The standard odors may be selected as desired according to the odor to be measured.

In the measurement of an unknown sample of interest, the unknown sample is supplied to the suction port 1, and is then drawn into the sensor cell 3 by the pump 4. Six detection signals produced by the odor sensors 31–36 are sent to the signal processor 8, where the signals are sent to the index calculator 84 via the peak detector 81.

The index calculator 84 performs the following operations: read out the data representing the plural standard odor curves from the standard odor coefficient memory unit 83; locate the measurement point P of the unknown sample within the six-dimensional space where the standard odor curves are formed; locate the points on the standard odor curves that give the minimum distances from the measurement point P to the standard odor curves, respectively; and calculate the minimum distances. Then, the degrees of similarity to the standard odors and the total odor intensity are calculated as described above. The olfactory thresholds of the standard odors should be measured and stored beforehand in the olfactory threshold memory unit 85.

The signal processor 8 displays the degrees of similarity and the odor intensity in an easy-to-understand form on the screen of the display 6. The degree of similarity obtained as described above takes a greater value when the concentration is high than when the concentration is low. One solution to this problem is to define the degree of similarity of a standard odor having the highest degree of similarity as 100 and to normalize the degrees of similarity to all the other standard odors. In this case, it is preferable to present the odor intensity separately because the normalized degrees of similarity represent the only the qualitative feature of the odor.

Figure 13:
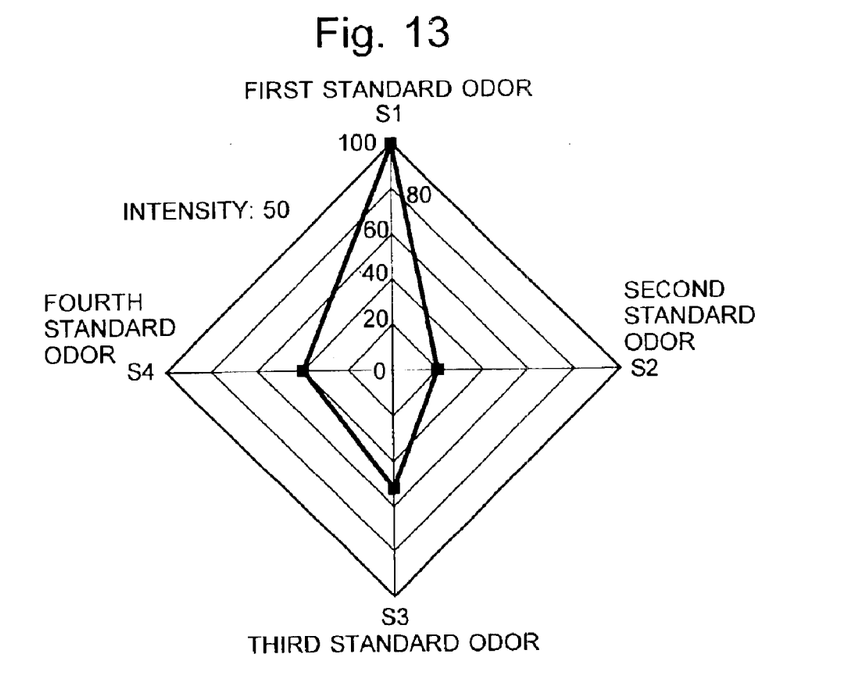
FIG. 13 illustrates the measurement principle of the apparatus of the second embodiment.

FIG. 13 shows an example of displaying the degrees of similarity and the odor intensity. In FIG. 13, the degrees of similarity to four standard odors are shown by a radar chart, and the odor intensity is separately displayed by characters and numerals ("INTENSITY: 50"). This is of course one of various methods of displaying the data. Such a visual output allows the user to easily understand what standard odor is the closest to the unknown odor and how close they are to each other, or how strong the odor is.

Thus, the odor measuring apparatus of the second embodiment calculates the degrees of similarity to plural standard odors and derives the odor intensity from the degrees of similarity. By showing the property (degree of similarity) and intensity of an unknown odor, the apparatus presents the qualitative and quantitative data of the unknown odor.

Example of Measurement 2

Figure 14:
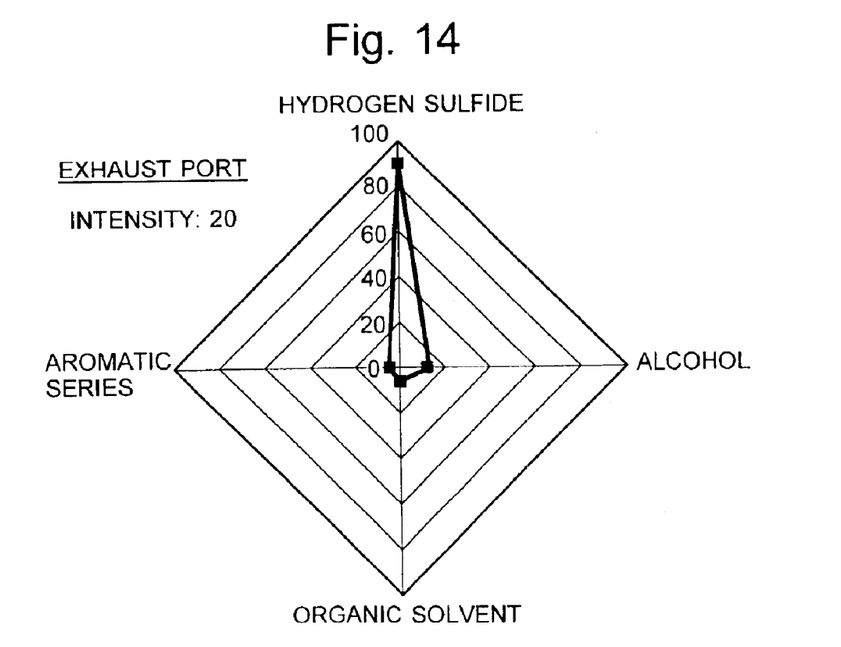
FIG. 14 shows an example of the results of measurements obtained by the apparatus of the second embodiment.
Figure 15:
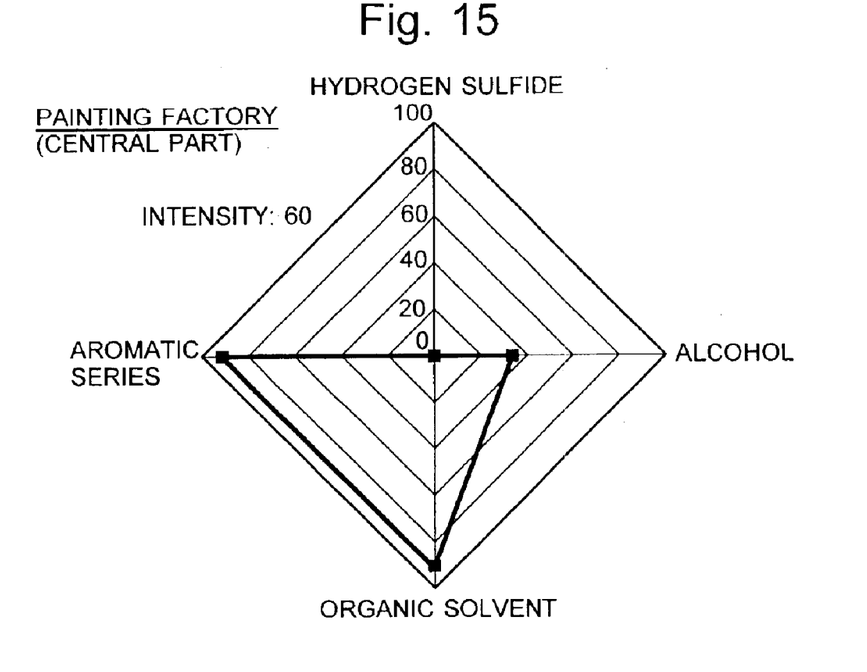
FIG. 15 shows an example of the results of measurements obtained by the apparatus of the second embodiment.
Figure 16:
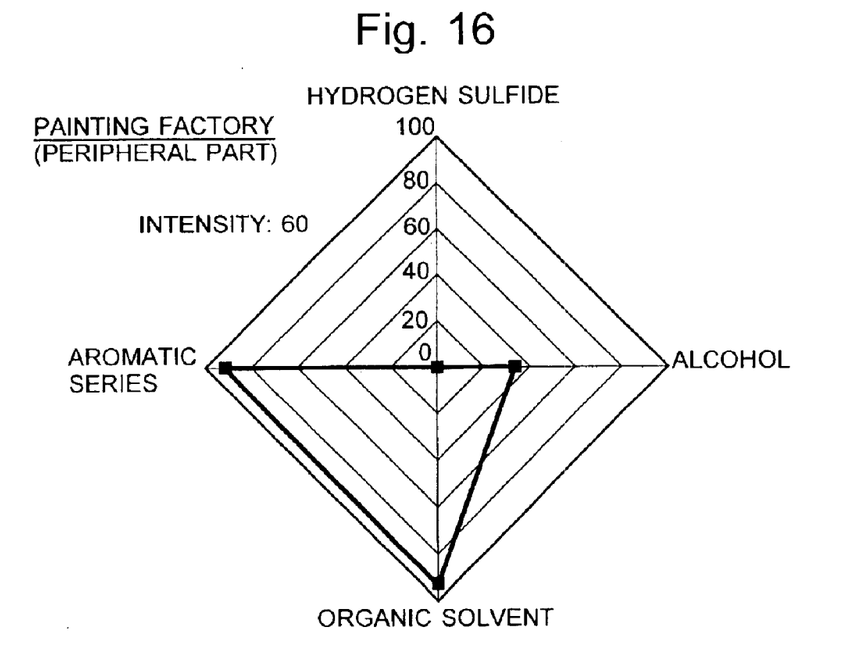
FIG. 16 shows an example of the results of measurements obtained by the apparatus of the second embodiment.

FIGS. 14–16 show examples of measurement by the odor measuring apparatus of the second embodiment. In this measurement, an aromatic series (e.g. toluene) and an alcohol (e.g. n-butanol) are used as the good standard odors, and a sulfur compound (e.g. methyl mercaptan) and an organic acid (e.g. butyric acid) are used as the bad standard odors.

FIG. 14 shows the result of a measurement of an odor taken at an exhaust port. The radar chart shows that the hydrogen sulfide is dominant. FIGS. 15–16 show the results of measurements of odors taken at the central part and the peripheral part of a painting factory, respectively. These results show that the organic solvent and the aromatic series are dominant. The radar charts of FIGS. 15–16 look almost identical, which means that the odors have almost identical quality. As regards the odor intensity, however, the intensity of the odor taken at the peripheral part is 20, while that of the odor taken at the central part is 60. This means that the odor is much stronger at the central part than at the peripheral part.

Thus, the odor measuring apparatus of the second embodiment can provide useful and easy-to-understand information to the user by quantitatively showing the similarity and intensity of the odor.

In the odor measuring apparatus of the first or second embodiment, it is convenient to store data on the date of measurement of the standard odors together with the standard odor vectors or the standard odor curves corresponding to the standard odors. As described above, when a measurement is practically performed with the odor measuring apparatus according to the present invention, it is necessary to measure many kinds of standard samples beforehand. For high accuracy of measurement, it is most desirable to measure necessary standard samples immediately before the measurement of an unknown sample to obtain the latest standard odor vectors or curves. This measurement, however, consumes so much time and labor that it is almost impossible to measure the necessary standard odors all at once. Therefore, it is often the case for the user to take several days to prepare the standard odor vectors or curves for each standard odor, or to find enough free time to prepare such vectors or curves with an odor measuring apparatus which is unused as yet. In such case, it is preferable to store the measurement date with the corresponding standard odor vectors or the standard odor curves. This allows the user to read out the latest standard odor vectors or curves immediately before the measurement of an unknown sample and use the latest data to calculate various indices and values relating to the odor.

It should be understood that the above embodiments are mere examples and may be changed or modified within the spirit and scope of the present invention.

What is claimed is:

1. An odor measuring apparatus, comprising:
   a) m pieces of odor sensors having different responsive characteristics, where m is an integer greater than one;
   b) an angle calculator for calculating an angle between an unknown odor vector and a standard odor vector in an m-dimensional space formed by a result of a measurement with the m pieces of odor sensors, where the unknown odor vector is represented by a result of a measurement of an unknown sample and the standard odor vector is represented by results of a plurality of measurements of a known standard odor; and
   c) an index calculator for calculating an index that represents a similarity of the unknown odor to the standard odor, where the index is calculated based on said angle.

2. The odor measuring apparatus according to claim 1, further comprising an intensity calculator for calculating an index relating to an odor intensity by a method including steps of taking an orthogonal projection of the unknown odor vector on the standard odor vector, deriving the odor concentration of the standard odor vector component of the unknown sample from the length of the orthogonal projection of the unknown odor vector, and calculating the index relating to the odor intensity.

3. The odor measuring apparatus according to claim 1, wherein the index calculator includes a corrector for correcting the index, taking account of a difference in sensitivity between the odor sensor and an olfactory sense of a human being.

4. The odor measuring apparatus according to claim 1, further comprising a storage unit for pre-storing results of measurements of n kinds of standard odors by the odor sensors, where n is an integer greater than one, or for pre-storing standard odor vectors represented by the results of the measurements.

5. An odor measuring apparatus, comprising:
   a) m pieces of odor sensors having different responsive characteristics, where m is an integer greater than one;
   b) a concentration point locator for locating a temporary point of concentration on a standard odor curve in an m-dimensional space formed by a result of measurement with the m pieces of odor sensors, where the standard odor curve is represented by a plurality of measurements of a known standard odor and the temporary point of concentration is located by a preset rule with respect to a measurement point representing a result of a measurement of an unknown sample; and
   c) an index calculator for calculating an index representing a similarity of the unknown odor to the standard odor, where the index is calculated based on a location of the temporary point of concentration in the m-dimensional space and on a value representing an index of proximity of the temporary point of concentration to the measurement point.

6. The odor measuring apparatus according to claim 5, wherein the concentration point locator locates the temporary point of concentration as a point on the standard odor curve where the distance from the measurement point is minimized; and the index calculator attenuates the concentration, derived from the location in the space of the temporary point of concentration, according to the distance between the temporary point of concentration and the measurement point or according to the angle between a standard odor line and an unknown odor line drawn on an assumption that each of the standard odor and the unknown odor changes along a straight line with respect to concentration, and calculates the index regarding the attenuated concentration as indicative of the contribution of the standard odor to the odor of the unknown sample.

7. The odor measuring apparatus according to claim 5, wherein the index calculator may preferably include a corrector for performing a correction account of a difference in sensitivity between the odor sensor and an olfactory sense of a human being, using a threshold of the olfactory sense of a human being.

8. The odor measuring apparatus according to claim 5, further comprising a storage unit for pre-storing results of measurements of n kinds of standard odors by the odor sensors, where n is an integer greater than one, or for pre-storing standard odor vectors represented by the results of the measurements.

9. The odor measuring apparatus according to claim 8, wherein the storage unit stores the standard odor curve in association with information about a measurement date of the standard odor, and the concentration point locator locates the temporary point of concentration on the standard odor curve by using a standard odor curve of the latest measurement date.

* * * * *